United States Patent [19]

Thomason et al.

[11] Patent Number: 5,507,758
[45] Date of Patent: Apr. 16, 1996

[54] INSERTABLE SUTURE GRASPING PROBE GUIDE, AND METHODOLOGY FOR USING SAME

[75] Inventors: Rodger Thomason, Los Angeles; James E. Carter, Mission Viejo; Mark J. Legome, Mission Viejo; Neil H. Naves, Mission Viejo, all of Calif.

[73] Assignee: Inlet Medical, Inc., Eden Prairre, Minn.

[21] Appl. No.: 139,637

[22] Filed: Oct. 19, 1993

Related U.S. Application Data

[63] Continuation-in-part of Ser. No. 112,585, Aug. 25, 1993.
[51] Int. Cl.$^6$ .................................................. A61B 17/00
[52] U.S. Cl. ........................... 606/148; 606/139; 604/280
[58] Field of Search ...................... 606/139, 148, 606/96, 98, 102; 604/264, 280, 239; 128/4

[56] References Cited

U.S. PATENT DOCUMENTS

| | | | |
|---|---|---|---|
| 3,361,382 | 1/1968 | Converse | 606/148 |
| 3,399,668 | 9/1968 | Lundgren | 604/280 |
| 3,577,991 | 5/1971 | Wilkinson . | |
| 4,345,602 | 8/1982 | Yoshimura et al. | 604/280 |
| 4,553,543 | 11/1985 | Amarasinghe | 606/148 |
| 4,621,640 | 11/1986 | Mulhollan et al. . | |
| 4,744,353 | 5/1988 | McFarland | 606/96 |
| 4,899,743 | 2/1990 | Nicholson . | |
| 4,938,214 | 7/1990 | Specht et al. . | |
| 4,950,273 | 8/1990 | Briggs . | |
| 4,955,384 | 9/1990 | Taylor et al. | 604/280 |
| 4,995,865 | 2/1991 | Gahara et al. | 604/280 |
| 5,015,250 | 5/1991 | Foster . | |
| 5,041,129 | 8/1991 | Hayhurst et al. . | |
| 5,053,043 | 10/1991 | Gottesman et al. . | |
| 5,078,721 | 1/1992 | McKeating . | |
| 5,100,417 | 3/1992 | Cerier et al. . | |
| 5,127,785 | 7/1992 | Faucher . | |
| 5,147,373 | 9/1992 | Ferzli . | |
| 5,171,256 | 12/1992 | Smith et al. . | |
| 5,171,257 | 12/1992 | Ferzli . | |
| 5,176,691 | 1/1993 | Pierce . | |
| 5,192,298 | 3/1993 | Smith et al. . | |
| 5,196,023 | 3/1993 | Martin . | |
| 5,201,743 | 4/1993 | Haber et al. . | |
| 5,201,744 | 4/1993 | Jones . | |
| 5,201,752 | 4/1993 | Brown et al. . | |
| 5,201,759 | 4/1993 | Ferzli . | |
| 5,220,926 | 6/1993 | Jones . | |
| 5,222,508 | 6/1993 | Contarini . | |
| 5,226,899 | 7/1993 | Lee et al. | 604/280 |
| 5,234,444 | 8/1993 | Christoudias . | |
| 5,269,772 | 12/1993 | Wick | 604/264 |
| 5,281,237 | 1/1994 | Gimpelson | 606/148 |
| 5,306,278 | 4/1994 | Dahl et al. | 606/96 |
| 5,334,200 | 8/1994 | Johnson | 606/148 |

*Primary Examiner*—Stephen C. Pellegrino
*Assistant Examiner*—Jeffrey A. Schmidt
*Attorney, Agent, or Firm*—Cislo & Thomas

[57] ABSTRACT

A surgical instrument, guide and method capable of being used for closure of peritoneum fascia, occlusion of bleeding vessels such as inferior epigastric, and for all uses related to accurately passing suture material through a guide into tissue with the tip of the surgical instrument in a standard suture/needle driving position with a sharp tip that opens and closes with the surgeon grasping suture material with the sharp tip and inserting the tip/suture through tissue until the tip is seen through the peritoneum by direct vision, wherein the suture is released by opening and withdrawing the tip from the guide, and recovered by using the guide to redirect the tip and puncturing the tissue opposite the first point of insertion wherein the tip grasps the suture and pulls the suture through the guide, and outside the wound providing for rapid closure of the surgical incision, and wherein a guide insertable within the wound to be closed guides the surgical instrument at a predetermined angle from the longitudinal axis of the guide.

15 Claims, 8 Drawing Sheets

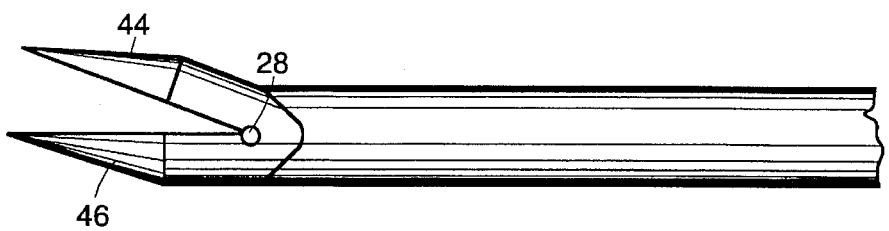
FIG. 7.
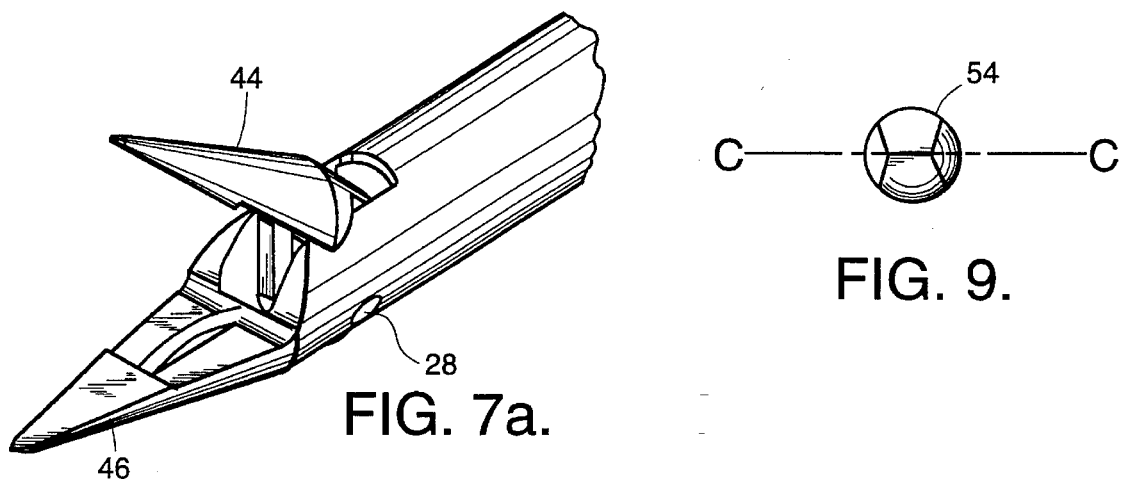
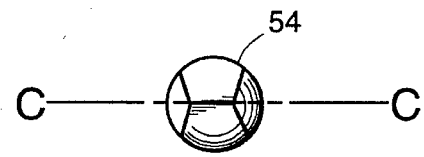
FIG. 9.
FIG. 7a.
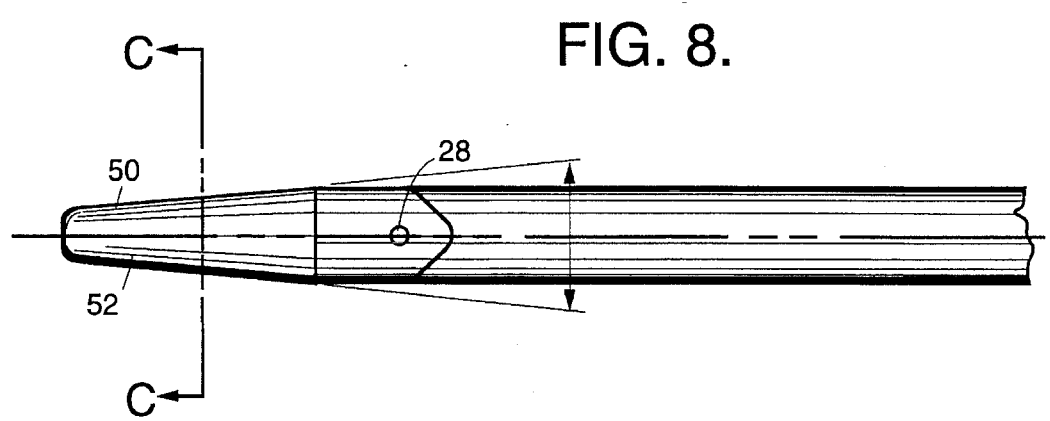
FIG. 8.
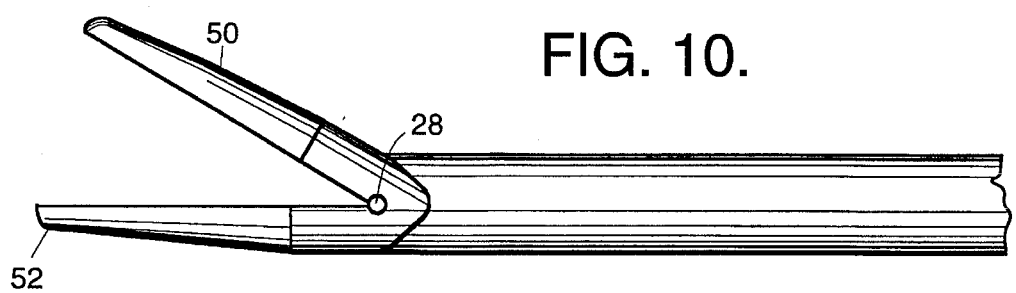
FIG. 10.

INSERTABLE SUTURE GRASPING PROBE GUIDE, AND METHODOLOGY FOR USING SAME

This is a Continuation-In-Part Application of an early filed U.S. application Ser. No. 08/112,585, filed on Aug. 25, 1993.

The present invention relates to improvements in the procedure for suturing tissue during endoscopic/laparoscopic surgery. More particularly, the invention relates to a method of suturing which utilizes a modified laparoscopic grasper and a guide.

An endoscopic/laparoscopy procedure involves making small surgical incisions in a patient's body for the insertion of trocar tubes thereby creating access ports into the patient's body. Thereafter, various types of endoscopic/laparoscopic instruments are passed through these access ports and the appropriate surgical procedures are carried out.

After the surgical procedure is performed the trocar tubes are removed and the incisions sutured closed by using both a needle and grasper for penetrating the tissue and handling the suture. This procedure for closure is frequently a time-consuming procedure requiring the identification of the fascia and closure of each fascial site with suture from an external point.

The necessity for closing these port sites in laparoscopic surgery is critical since suturing the incisions improperly can lead to bowel herniation through the port sites as well as the possibility of omental trapping if the fascial sites are not properly closed. Incisional hernias have occurred in both laparoscopic-assisted vaginal hysterectomies and laparoscopic cholecystectomies as well as other advanced laparoscopic procedures.

Thus, there is a need for an endoscopic/laparoscopic instrument and method which will significantly reduce the operating time and is better able to give the surgeon direct visualization of the fascial and peritoneal closing. Additionally, there is a need for a surgical instrument which allows the surgeon to control bleeding sites by rapidly putting sutures around blood vessels of the abdominal wall.

Furthermore, there is a need to accurately and consistently guide and orient an endoscopic/laparoscopic instrument into proper position to accurately and easily provide for placement and retrieval of suture materials within an open wound to be closed.

The subject invention herein solves all of these problems in a new and unique manner which has not been part of the art previously. General types of surgical forceps and laparoscopic graspers and guides are known in the art and some related patents directed to surgical instruments or guides are described below:

U.S. Pat. No. 5,192,298 issued to W. Smith et al. on Dec. 15, 1992

This patent is directed to a disposable laparoscopic surgical instrument. The laparoscopic surgical instrument comprises a tube surrounded by a peripheral insulating shrink wrap layer, a clevis means, and effectors pivotally engaged to the clevis at a pivot pin, and activating means. The effectors are provided with blades or graspers which taper to a point and are rotatably mounted on the pivot pin.

U.S. Pat. No. 5,201,743 issued to T. Haber et al. on Apr. 13, 1993

This patent is directed to an axially extendable endoscopic surgical instrument. The endoscopic surgical instrument includes an elongate body, a tip carrier tube, a tip assembly removably mounted to the distal end of the carrier tube and having a pair of movable jaws, a driver assembly which causes jaws to move between open and closed positions, and a jaw rotating assembly which causes the tip assembly and jaws therewith to rotate about an axis. The jaws taper substantially at their distal ends and the interior surface of the jaws are serrated.

U.S. Pat. No. 4,950,273 issued to J. M. Briggs on Aug. 21, 1990

This patent is directed to a cable action instrument. The instrument comprises a controller, a reaction end, and an angle adjustment section which connects the controller to the reaction end, and a flexible control cable assembly extending between the controller and the reaction end. The reaction end consists of a scissors tip having a stationary blade and a cable activated blade, both of which have pointed distal ends. A forceps instrument tip having a stationary plant arm and a cable activated arm may be substituted for the scissors tip.

U.S. Pat. No. 4,938,214.issued to P. Specht et al on Jul. 3, 1990

This patent is directed to a hand-held surgical tool. The surgical tool includes an operating end having first and second blade tips which are movable between open and closed positions. When the blade tips are closed, the surgical tool has a needle sharp point having a diameter of only about 50 microns to 2 mm.

U.S. Pat. No. 3,577,991 issued to G. R. Wilkinson on May 11, 1971

This patent is directed to a sewing tissue instrument. The forceps are pivoted together with the outer jaws and a spring set between the members. The thread slides to the end of the forceps and the free end of the thread is pulled through the loops to make a knot.

U.S. Pat. No. 5,196,023 issued to W. Martin on Mar. 23, 1993

This patent is directed to a surgical needle holder and cutter wherein the cutter forming the upper part of the blade has a concave shape. When the forcep jaw is opened, an approximately elliptical opening is formed between the ridge or cutter and the depression into which a thread may be brought from the direction of the opening of the forceps jaw and then can be cut off by closing the jaw.

U.S. Pat. No. 5,222,508 issued to O. Contarini on Jun. 29, 1993

This patent is directed to methods for closing punctures and small wounds of the human body, allowing such punctures to be sutured and closed with an internal seal. Before the trocar is removed, a suture insertion means, a needle preferably of stainless steel, having an eyelet or a slot or barb to retain the suture material, is pushed completely through the skin and subcutaneous layer. A retrieval means is inserted adjacent the puncture so its barbed portion grasps or snares the free end of the suture material. The insertion needle, retrieval needle, and trocar are withdrawn and the suture drawn tight.

U.S. Pat. No. 5,053,043 issued to J. Gottesman et al on Oct. 1, 1991

This patent is directed to a suture guide with interchangeable tips for placing sutures in the severed end of a body duct. Various tips having one or more apertures and channels for placing sutures are provided to screw into an elongate member. The elongate member has a handle at the opposite end. This guide is particularly useful for the placement of sutures into the urethral stump.

U.S. Pat. No. 5,201,744 issued to M. W. Jones on Apr. 13, 1993

This patent is directed to a method and device for suturing using a rod with a needle holder. This device, a knot tier instrument, has a rod with an end having notches for guiding suturing threads, and a slot for holding a needle. The end may be magnetized to aid in magnetically holding the needle in the slot. A hollow cannula or access tube can be inserted through the skin, and the knot tier inserted into the cannula for suturing the wound closed.

U.S. Pat. No. 5,176,691 issued to J. Pierre on Jan. 5, 1993

This patent is directed to a plurality of embodiments of knot pushers formed from elongated rods. The pusher with an elongated rod has various configurations to guide suture ends and push the knot. The end of the rod has a face shaped to push the knot, and near the edges of the rod are eyelets or grooves or the like to guide the sutures as the knot is being pushed. The device is to advance the knob of a suture through an endoscope portal or a cannula or the like.

U.S. Pat. No. 4,621,640 issued to J. S. Mulhollan on Nov. 11, 1986

This patent is directed to a mechanical needle carrier which can grasp and carry a surgical needle through a cannula, position the needle, and set a stitch at a remote location, then release the needle for withdrawal from the cannula. The mechanical needle carrier is inserted through the cannula and a pivotal needle carrying head is positioned by adjusting knurled knobs so as to position the needle as required. Once the needle is set, it can be released and then retrieved by forceps or the like. This mechanical needle carrier provides the structure for suturing in a restricted field with the manipulation remote from the location of the needle.

SUMMARY OF THE INVENTION

The present invention is directed to a suturing method using an improved laparoscopic surgical instrument which permits a surgeon to pass suture without trauma through tissue while retaining the function of grasping the suture. The laparoscopic surgical instrument comprises a modified laparoscopic grasper wherein forcep jaws at the tip are manipulated by means of scissor type handles extending laterally from a tubular housing with an enclosed reciprocating actuating rod connected respectively with the scissor lever arms.

The laparoscopic surgical instrument of the present invention has the tip of the forcep jaws modified to have either a knife, chisel, or cone shaped tip when the jaws are in the closed position. These tips are configured such that they are needle sharp which is critical in reducing trauma and accompanying bleeding and further decreases tissue damage during the suturing procedure.

Another object of the invention is to provide a surgical method for the closure of a surgical incision under direct camera laparoscopic vision of the surgeon, and the closure that is accomplished is a mass closure which allows for closure of peritoneal surfaces as well.

A further object of the invention is to provide a laparoscopic instrument that allows for the rapid control of bleeding from inferior epigastric lacerations or other lacerations of vessels in the outer (or abdominal) wall that may occur with placement of the laparoscopic trocars.

Another object of the invention is to provide a laparoscopic instrument that easily disassembles at the handle and at the interface between the tube member and handle for providing easy access to all the instrument components for cleaning and sterilization prior to surgery.

Still another object of the invention is to provide a laparoscopic instrument having a pair of independently operated actuatable means such that a single instrument can simultaneously perform both the functions of a needle and grasper during laparoscopic surgery.

Yet another object of the present invention is to provide a surgical instrument that works in a similar manner to a needle driver without the requirement for the needle itself in passing suture easily through the fascial and peritoneal surfaces and for retrieving the suture for completing the suture procedure in a rapid, safe and visualized manner.

It is another object of the invention to provide a guide to accurately and consistently restrain the position and angle of insertion of a laparoscopic instrument to provide for proper placement and retrieval of suture material at a predetermined location within the body.

Accordingly it is an objective of the present invention to provide a method associated with an improved surgical instrument of the standard laparoscopic type grasper that better suits the need of a surgeon for suturing closed a surgical incision and guiding the grasper. In addition, it is the objective of the present invention to allow the accurate passage of suture through tissue to a predetermined level within the body in order to suture or ligate vessels, approximate tissues and perform all suturing that would require a separate needle driver in laparoscopic surgery. The improvements afforded by this instrument and method will be set forth throughout the following description, claims and accompanying drawings.

BRIEF DESCRIPTION OF THE DRAWINGS

The above, as well as other, advantages of the present invention will become readily apparent to those skilled in the art from the following detailed description of the preferred embodiments when considered in the light of the accompanying drawings in which:

FIG. 7 is a side elevation view, partly in section, of the forcep jaws of FIG. 5 in a completely open condition.

FIG. 8 is a side elevation view, partly in section, of the forcep jaws having a knife shaped tip.

FIG. 9 is a cross-sectional view taken along the line C—C in FIG. 8.

FIG. 10 is a side elevation view, partly in section, of the forcep jaws of FIG. 8 in a completely open condition.

DESCRIPTION OF THE PREFERRED EMBODIMENTS

Figure 1:
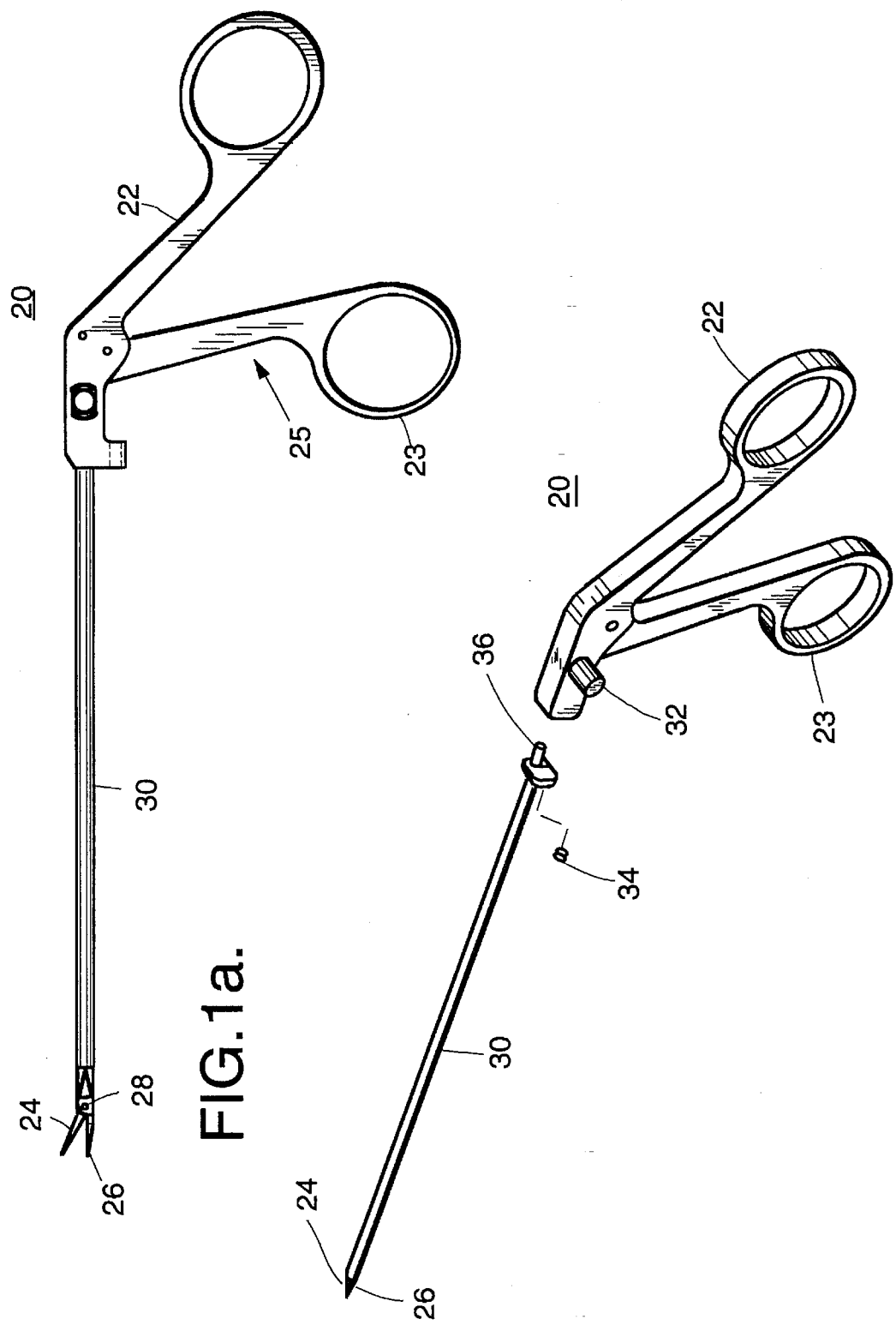
FIG. 1A is a side elevational view of the laparoscopic instrument of the present invention.
FIG. 1B is an exploded side elevational view of the laparoscopic instrument of of FIG. 1A.

Referring now to the drawings wherein like reference numerals refer to like and corresponding parts throughout, the laparoscopic instrument is generally indicated by numeral 20. Referring now to FIGS. 1A and 1B, forcep jaws 24 and 26 are pivoted back and forth in double action movement about an axis defined by pivot pin 28 when actuating rod 36 is reciprocated by a surgeon manipulating the scissor handles 22 and 23 providing a driving means 25 for driving forcep jaws 24 and 26 in a closed position through a patient's skin. Detachable means 27 comprise an elongated tube 30 concentrically sharing an axis with the actuating rod 36 having forcep jaws 24 and 26 engaged at a distal end.

As shown in FIG. 1B, the laparoscopic instrument 20 may be easily disassembled for sterilization prior to surgery in separating driving means 25 from detachable means 27 by loosening the knurled screw 34 on fixed handle housing 22 and rotating the elongated tube 30 and forcep jaws 24 and 26 slightly, unlatching hook 31 from pin 37 which thereby frees actuating rod 36 and tube 30 from handle housing 22. By loosening thumb screw 35, movable handle or lever means 23 can be disassembled from fixed handle housing 22 that allows for cleaning of the inside of the handle housing area. When dissembled the parts may be flushed, washed and dried according to hospital procedures for stainless steel surgical instruments. A cleaning port 32 may be provided for ease in flushing the disassembled fixed handle housing 22.

Figure 2:
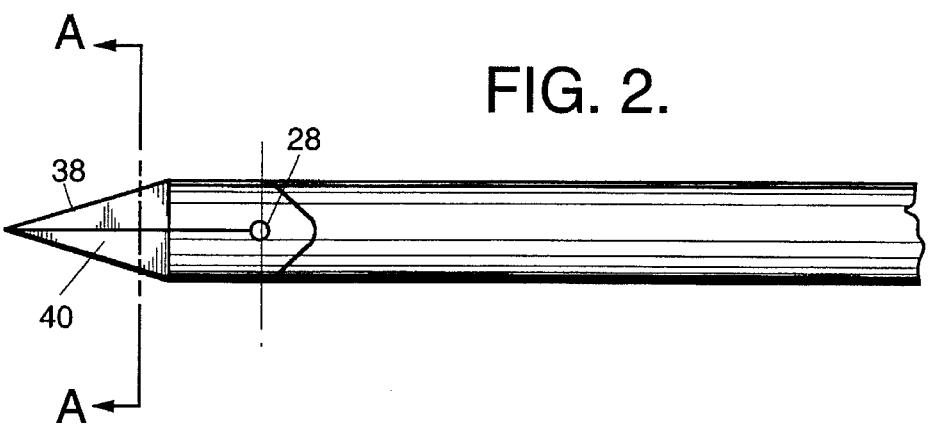
FIG. 2 is a side elevation view, partly in section, of the forcep jaws having a chisel shaped tip.
Figure 3:
FIG. 3 is a cross-sectional view taken along the line A—A in FIG. 2.
Figure 4:
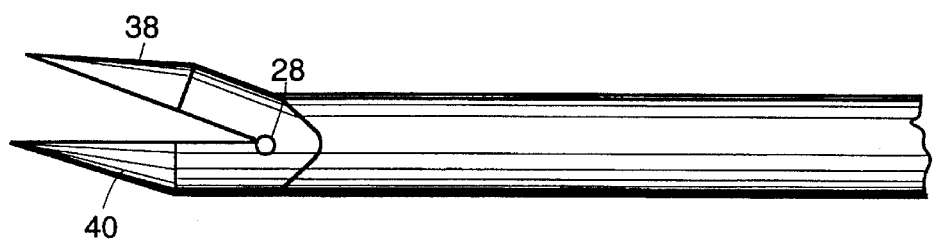
FIG. 4 is a side elevation view, partly in section, of the forcep jaws of FIG. 2 in a completely open condition.

With the above described arrangement, it will be seen that the surgeon is able to selectively operate the scissor handles 22 and 23 to independently open and close the movable forcep jaw 24 in relationship to fixed forcep jaw 26 for grasping, carrying or releasing suture during a laparoscopic operation. To open forcep jaw 24, the surgeon moves movable handle or lever means 23 forward toward the distal end of tube 30. As shown in FIGS. 2 and 3, the forcep jaws 24 and 26 have a chisel shape 38 and 40 which when closed form a chisel shape tip 42. This chisel shape tip 42 operates as a sharp needle point that simultaneously grips and passes the suture through soft tissue. Referring to FIG. 4, chisel shaped jaw 38 pivots open and closed about pivot pin 28 and chisel shaped jaw 40 which is fixed and non-pivotable.

Figure 6:
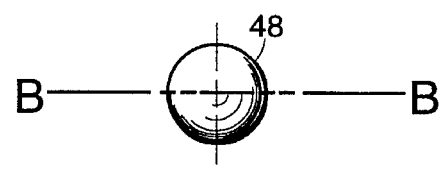
FIG. 6 is a cross-sectional view taken along the line B—B in FIG. 5.
Figure 5:
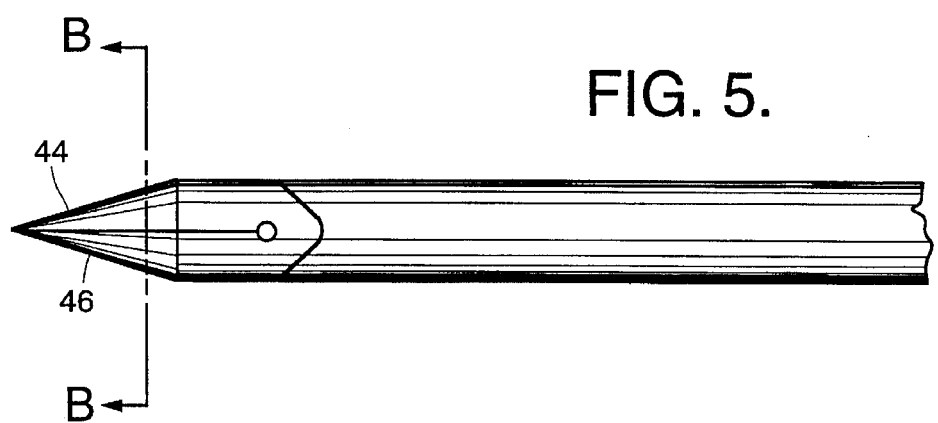
FIG. 5 is a side elevation view, partly in section, of the forcep jaws having a cone shaped tip.

Although the forcep jaws are shown as chisel shaped in FIGS. 2 and 3, they may alternatively have a cone shape 44 and 46 forming a cone shaped tip 48 as shown in FIGS. 5 and 6. Referring to FIG. 7, cone shaped jaw 44 also pivots open and closed about pivot pin 28 and cone shaped jaw 46 which is fixed and non-pivotable. Alternatively, the aforementioned forcep jaws may have a knife shape tip 20 and 52 forming a knife shaped tip 54 as shown in FIGS. 8 and 9. Likewise, as shown in FIG. 10, the knife shaped jaw 50 pivots open and closed about pivot pin 28 and knife shaped jaw 52 which is fixed and non-pivotable. In all the above views, the tips are required to be sharp which is critical in reducing trauma and accompanying bleeding and to decrease tissue damage during the suturing procedure.

Figure 11:
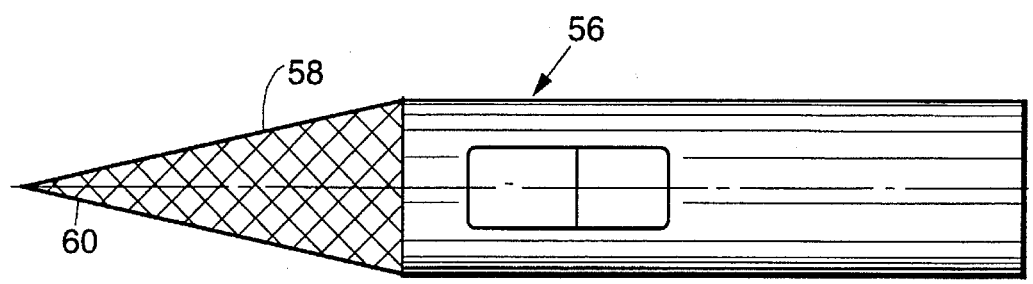
FIG. 11 is a top planar view of the bottom forcep jaw according to one embodiment of the invention.

Common to the various shaped jaw embodiments is a generally partial crosshatched interior jaw surface 58 embedded in jaw body 56 as shown in FIG. 11 which facilitates in grasping more securely the suture material 66 during insertion into tissue. In order to maintain the sharpness of the tip, a partial nonhatched area 60 is provided at the forward end of jaw body 56.

Figure 12:
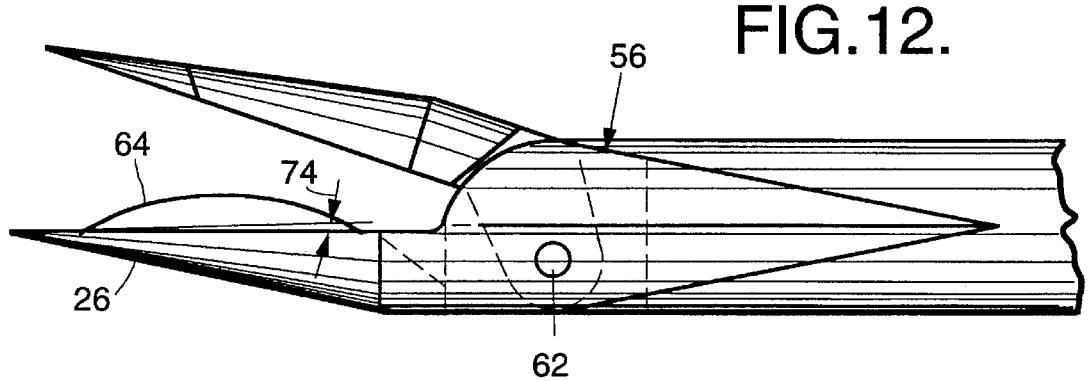
FIG. 12 is a side elevational view, partly in section, of the forcep jaws according to one embodiment of the invention.
Figure 13:
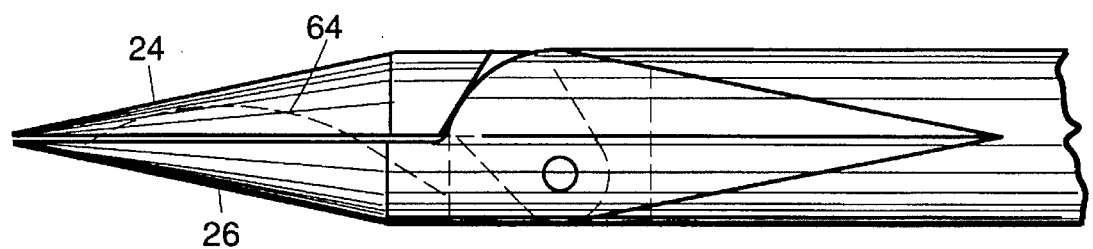
FIG. 13 is a side elevational view, of the forcep jaw of FIG. 12 in a completely closed position.
Figure 13A:
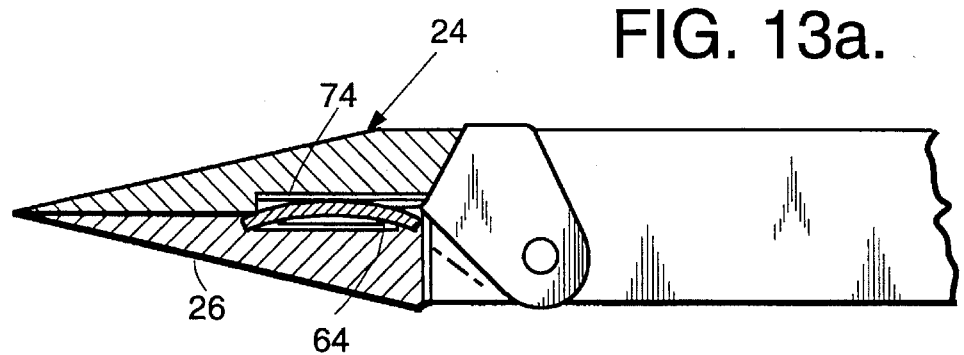

FIGS. 12 and 13 show another embodiment of a means to retain the sharpness of the tip at the end of jaw body 56 when the forcep jaws are closed. In FIG. 12 it is seen that lower forcep jaw body 26 is inclined by a small angle, indicated at 74, towards pivot pin hole 62. With this arrangement the small angle 74 accounts for the thickness of the suture such that when the jaws are closed a sharp tip is still defined with the suture grasped resulting from the clearance provided by small angle 74. Additionally, a spring 64 is provided which has one end affixed into jaw body 26 at a point near pivot pin hole 62. The spring 64 assists in more firmly grasping the suture material by adding a compression force resulting in a more positive grip when the jaws 24 and 26 are closed as shown in FIG. 13. The spring 64 is especially useful in handling suture material that is large in diameter, therefore allowing for a wider range of suture sizes that can be used during surgery.

These features and their advantages in use will be more particularly appreciated when reviewing the following method of the present invention used to pass suture through soft tissues during endoscopic/laparoscopic surgery for which the instrument 20 of this invention is provided. In application the surgical instrument 20 is to be grasped by a skilled laparoscopic surgeon and placed for closure of punctured vessels in the abdominal wall or for closure of the fascia.

Figure 14A:
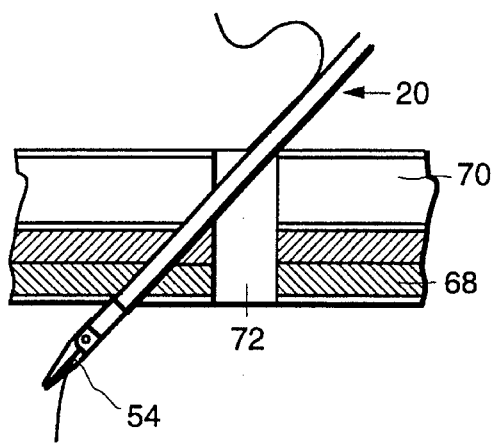
FIG. 14A is a diagrammatic sketch, partly broken away of the tip of the surgical instrument in the closed position passing suture through tissue.
Figure 14B:
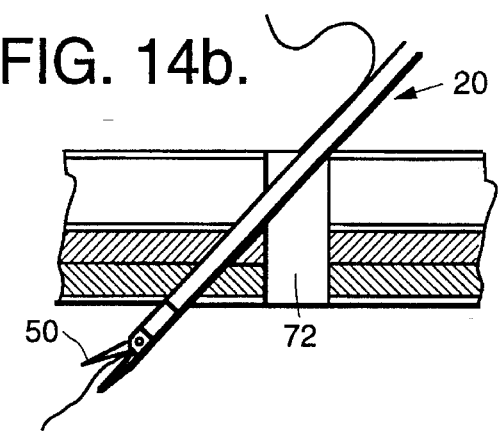
FIG. 14B is a diagrammatic sketch, partly broken away of the tip of the surgical instrument in the open position for dropping the suture.
Figure 14C:
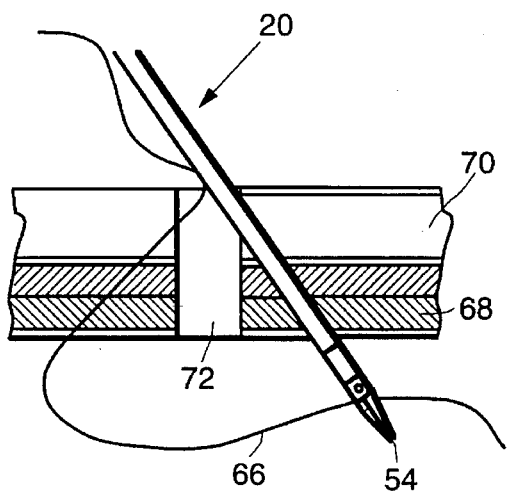
FIG. 14C is a diagrammatic sketch, partly broken away of the tip of the surgical instrument in the closed position passing through tissue at the other side of the incision and picking up suture.
Figure 14D:
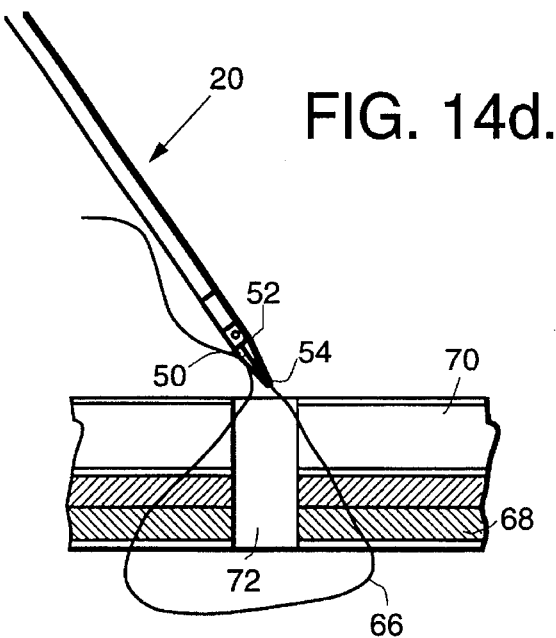
FIG. 14D is a diagrammatic sketch, partly broken away of the tip of the surgical instrument pulling suture through muscle fascia and peritoneum.
Figure 14E:
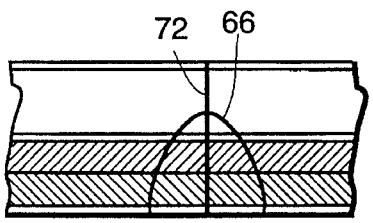
FIG. 14E is a diagrammatic sketch, partly broken away of the suture tied below the skin to complete closure.

FIGS. 14A through 14E are diagrammatic representations of one example of using the method and laparoscopic instrument 20 with the knife shaped tip 54 of the present invention grasping and passing suture through soft tissue for closure of an incision 72. In FIG. 14A the surgeon grasps the suture material 66 with tip 54 and inserts instrument 20 carrying suture material 66 through the muscle fascia 70 and peritoneum 68 until the tip 54 is seen through the peritoneum by direct camera vision. Subsequently, the surgeon releases the suture 66 by opening jaw 50 and withdrawing the instrument 20 out of incision 72 as shown in FIG. 14B. In FIG. 14C the surgeon then takes instrument 20 and inserts the tip 54 through the muscle fascia 70 and peritoneum 68 opposite the first point of insertion grasping the suture 66 with jaws 50 and 52 and pulls the suture 66 carried and held by tip 54 outside incision 72 as shown by FIG. 14D whereupon suture 66 is tied below the skin to complete closure of incision 72 as shown by FIG. 14E.

It is to be pointed out that the knife shaped tip 54 in the above described method may be replaced with either the chisel shape tip 42 or cone shaped tip 48. Although not shown, it may be envisioned in the above described method that a second surgical instrument 20 may be inserted through the muscle fascia 70 and peritoneum 68 opposite the first point of insertion grasping the suture 66 with jaws 50 and 52 and pulling the suture 66 held by tip 54 outside incision 72 by either an assistant or the surgeon resulting in a savings of time for completion of the closure.

By way of example but not of limitation, it has been shown that by using the present invention during a laparoscopic assisted vaginal hysterectomy, the total time required for the closure of the two 12 mm and one 10 mm trocar ports has been reduced from 15 minutes (as required by prior surgical procedures) to 3 minutes.

Figure 20A:
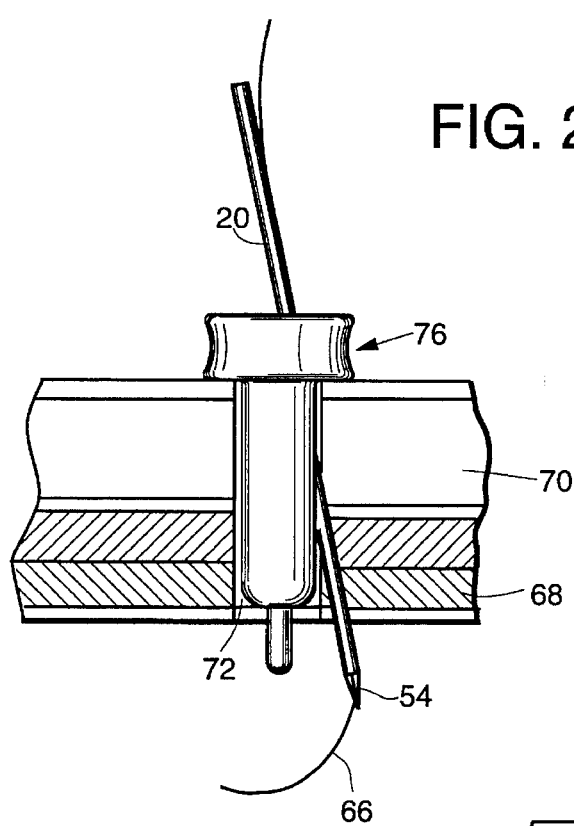
FIG. 20A is a diagrammatic sketch showing the guide of the present invention placed within the wound to be closed receiving the tip of a point of a surgical instrument received within a passageway carrying suture material.
Figure 20B:
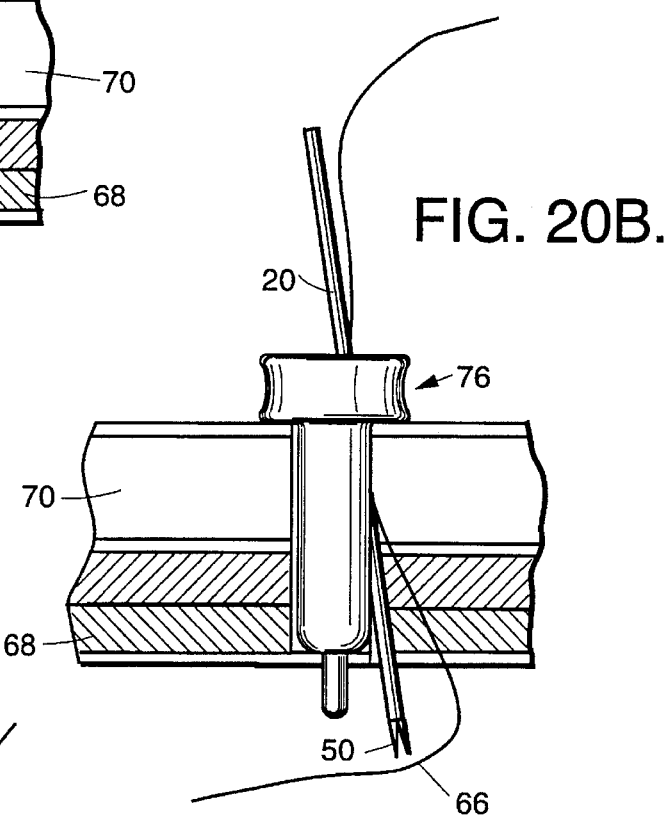
FIG. 20B is a diagrammatic sketch of the guide shown in FIG. 20A with the surgical instrument releasing the suture material.
Figure 20C:
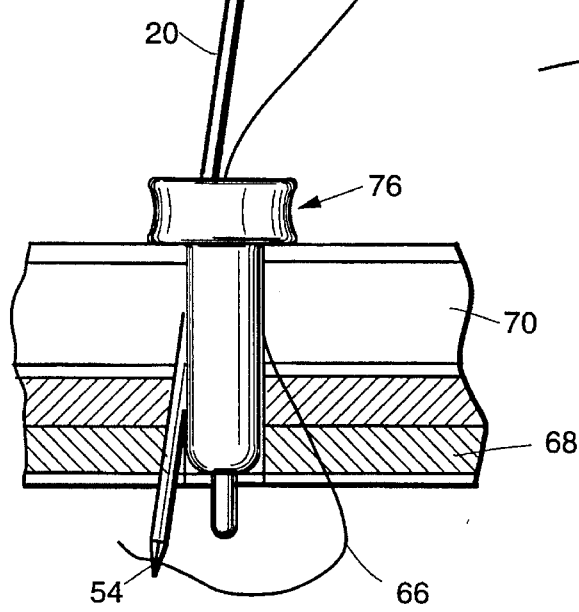
FIG. 20C is a diagrammatic sketch showing the guide of FIGS. 20A and 20B with the surgical tool being received in an opposite and adjacent passageway of the guide retrieving the suture material.

As shown in FIGS. 15–19, a specially adapted guide 76 can be used in the suturing procedure discussed above, and its application is demonstrated in FIGS. 20A–20C. The guide 76 provides the surgeon a device and methodology for accurately and precisely positioning and removing the suture material 66 in or from the patient's body where desired.

Figure 15:
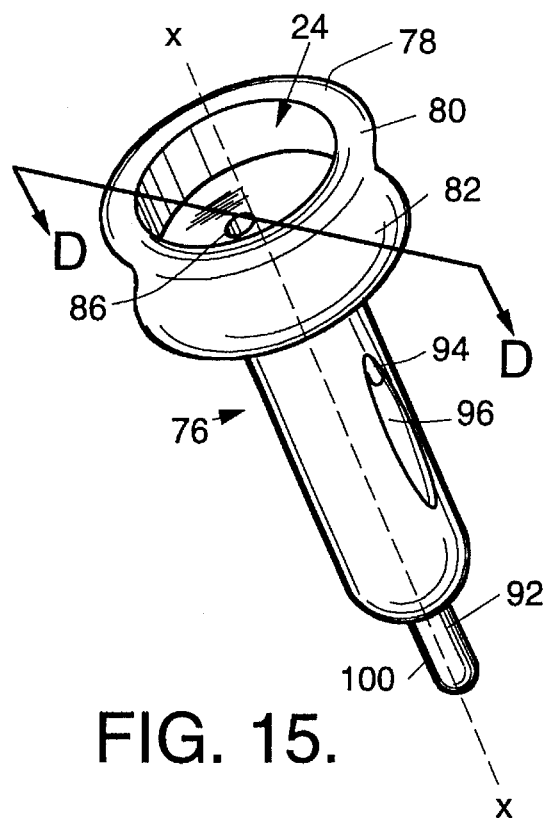
FIG. 15 is a perspective view of the insertable grasping probe guide of the present invention having a longitudinal axis x.

The guide 76 has a longitudinal axis x shown in FIG. 15 and is generally symmetrical about its x axis. Its proximal end 78 defines an integrally-formed annulus 80 which serves as a gripping area for the surgeon with a concave radially disposed surface 82 which further assists the surgeon in gripping and holding the guide 76. The concave surface 82 may be smooth or knurled.

A top cylindrical recess 84 in the annulus 80 exposes two entry holes 86 to generally linear passageways 88 through the guide 76. The passageways 88 are appositely adjacent and each forms a diverging angle alpha of approximately 10° with the longitudinal axis x, but can range over a number of angles less than 90°. Optimally, the angle is 9.6° for an overall guide 76 length of 2.7 inches. The entry holes 86 are located along a diameter line and are approximately 0.2 inches from center hole to center hole, but may vary between 0.1 inches to 1 inch depending upon the desired angle x. The holes are sized to receive the surgical instrument to be used.

In use the annulus 82 stands proud of the wound, but has an undersurface or lip 90 which is adjacent the wound to be sutured. The recess 84 provides access to the entry holes 86 and passageways 86, yet prevents unwanted body fluids from obscuring the entry holes 86. The lip 90 prevents the guide 76 from sliding into the wound, and therefore should be sized to be a greater diameter than the open wound to be sutured.

A proximal portion 92 of the guide 76 may be slightly tapered, although it may not be necessary. Tapering allows for greater ease of insertion into the wound. The passageways 88 have exit holes 94 in the proximal portion 92 and may include a flaring 96 or tapering. The holes 86 and 94 to passageways 88 are sized to receive the surgical tools to be used, and optimally may be less than one-quarter inch in diameter.

An extending finger 98 is adjacent the proximal portion 92 and primarily serves as an alignment or bearings indicator for the surgeon viewing the procedure by camera. It is helpful to actually see the relative positioning of the guide 76 by its extending finger 98 which extends far enough down to where the viewing is taking place during the operation. It is round on its proximal end 100 for ease of insertion.

An indice 102 may be located between the two entry holes 86 to visually advise the surgeon to line up the indice 102 with the cut of the wound to ensure that suturing takes place at approximately 90° to the sliced walls of flesh.

The entire guide 76 can be integrally molded out of high density polyethylene or other comparable material which is durable and medically inert or machined from stainless steel.

Figure 16:
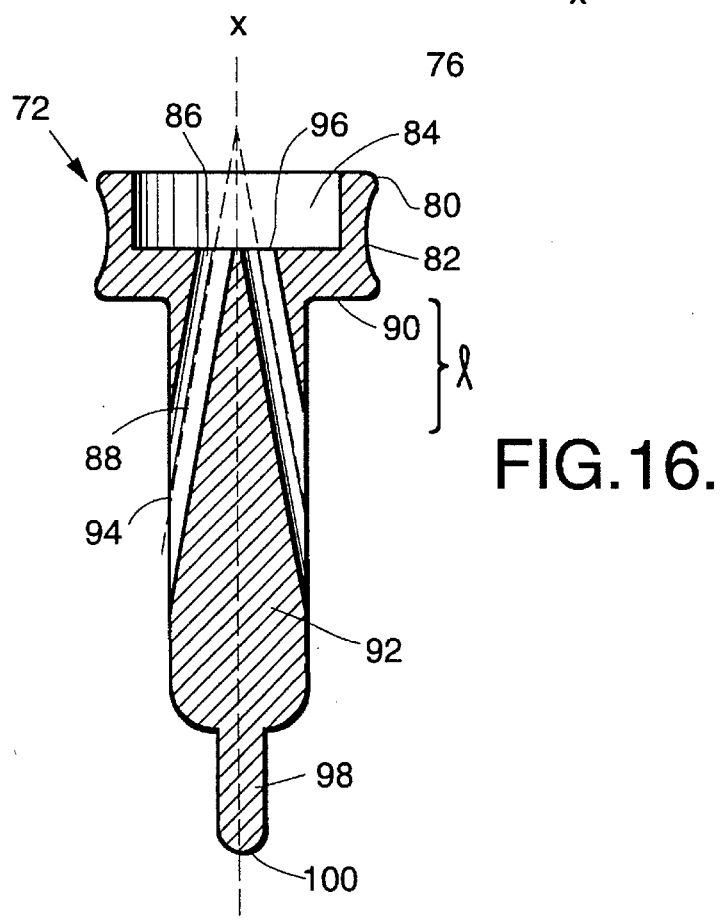
FIG. 16 is a cross-sectional view of the guide taken along the line D—D in FIG. 1 and FIG. 18.
Figure 18:
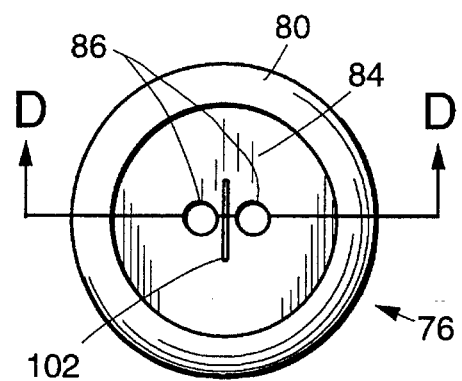
FIG. 18 is a top plan view of the guide shown in FIGS. 15, 16 and 17.
Figure 17:
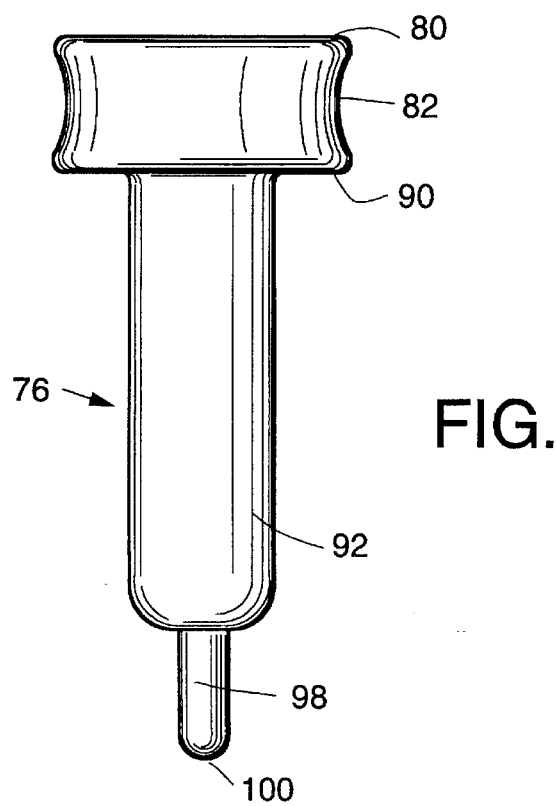
FIG. 17 is a side elevational view of the guide shown in FIGS. 15 and 16.
Figure 19:
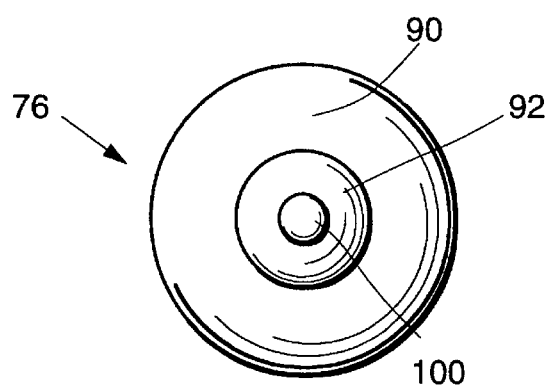
FIG. 19 is a bottom plan view of the guide shown in FIGS. 15, 16, 17 and 18.

The distance L as shown in FIG. 16 between the undersurface 90 of the annulus 80 and the exit holes 94 in the proximal portion 92 is a function of the patient's anatomy, in particular his or her body fat composition. Ideally, the surgeon desires to reach a particular layer to suture which may vary from patient to patient. Therefore, varying sized guides 76 are anticipated with the length L being different, and ranging between 0.5 inches and 2 inches. Also, the overall length of the proximal portion 92 may vary depending upon the patient's anatomy, but an optimum length ranges between 1.5 to 4 inches.

It is also possible to use the guide 76 of the present invention with only one passageway 88, however the surgeon would have to rotate the guide 76 180° to retrieve the suture material once the suture material was deposited.

As can be seen in FIGS. 20A–20C, the guide greatly assists in the procedure described above for FIGS. 14A–E. More particularly, the guide 76 is placed with the proximal end 92 through the skin incision, muscle, fascia, and peritoneum so that the finger 100 appears in the view of the laparoscope. The guide 76 is oriented so that the holes 86 in the guide 76 are in the caudad-to-cephalad position.

The fascial closure instrument 20 is inserted with suture in its grasp through the cephalad hole in the guide 76 and observed to exit through the peritoneum by laparoscopic view.

The suture is then released and the instrument 20 withdrawn from the guide 76. The instrument 20 is placed in the caudad hole of the guide and watched by laparoscopic view to exit through the peritoneum in the caudad position, therefore passing through fascia and peritoneum on the caudad side of the incision. The guide 76 is then withdrawn up on the shaft of the instrument 20, allowing the instrument free mobility to grasp the suture that had been left with the first passage.

The suture is withdrawn through the hole made by the instrument 20. The guide 76 is then withdrawn from the suture completely. The suture is then tied by standard techniques, thus encompassing the fascia and peritoneum in a mass closure under the skin.

The guide 76 allows the suture instrument through fascia and peritoneum and mass closure of all incisions greater than 7 mm, and the identification of the position of a trocar placement for use in occluding a trocar site.

It also provides for placement in a trocar or other abdominal wall site where a vessel such as an inferior epigastric has been lacerated to all passage of the instrument 20 for suturing of tissue around the vessel to occlude the vessel and stop bleeding, and for fascial closure of any abdominal incision.

It provides for a method to obtain a measured amount of fascia and peritoneum for laparoscopically controlled mass closure by varying the length of the tool and the angle of the guide holes. By varying the tip length and the length of the overall guide visualizing the guide 76 itself, and placing the guide properly in incisions intra-abdominally, closure of wounds in any weight individual is made possible.

By providing for the tip design, visualization of the guide 76 through the fascia and peritoneum is possible by laparoscopic visualization. It is most helpful for attaching soft tissue to the abdominal wall and fascia for support of any soft tissue structures, and for repair of vascular damage to abdominal wall in any area.

There has been described and illustrated herein an improved laparoscopic instrument and surgical method. While particular embodiments of the invention have been described, it is not intended that the invention be limited exactly thereto, as it is intended that the invention be as broad in scope as the art will permit. The foregoing description and drawings will suggest other embodiments and variations within the scope of the claims to those skilled in the art, all of which are intended to be included in the spirit of the invention as herein set forth.

What is claimed is:

1. A device for accurately guiding and positioning a surgical instrument bearing suture material to a predetermined area within the body for closing an open wound, comprising: a guide means having a longitudinal axis and distal and proximal ends, and further having a depth-limiting extending lip near said distal end of said guide means and being generally perpendicular to said longitudinal axis, wherein said proximal end is for insertion into the wound to a depth limited and determined by said extending lip, said guide means defining therein at least one generally linear passageway therethrough at a first diverging angle less than 90° from said longitudinal axis, and providing for exit holes above and below said lip, wherein said proximal end of said guide is tapered and positionable within said wound with the lip portion above the wound to be closed and the surgical instrument carrying suture material passed through said passageway at said angle to the predetermined area within the body to assist in closing the open wound.

2. The device of claim 1 further comprising a second passageway through said guide means forming a second angle less than 90° from said longitudinal axis, and positioned appositely adjacent said first passageway, and further having second exit holes above and below said lip, wherein the suture material can be left at the predetermined point within the body and the surgical tool and be inserted into one of said second exit holes above said lip portion through said second passageway to retrieve the suture material from the area within the body.

3. A device of claim 2 comprising an extending finger adjacent to said tapered end and generally symmetrical about said longitudinal axis extending a length sufficient to be accurately viewed and identified to provide a reference point while viewing any suturing procedure, and wherein said proximal end is downwardly tapered symmetrically along said longitudinal axis for ease of insertion.

4. A device of claim 2 wherein said distal end has a concave radial surface about said guides means' longitudinal axis to assist in gripping and positioning said guide means within the open wound.

5. A device of claim 2 wherein said exit holes in said proximal portion are of sufficient longitudinal distance from said lip to accommodate the depth of the wound to be closed and the particular tissue layer to be sutured, approximately in the range of 0.5 to 2 inches.

6. A device of claim 5 wherein said guide means available is a plurality of sizes having different radial diameters and different longitudinal lengths between said lip and said exit holes in said proximal end to accommodate the depth of the wound to be closed, the particular tissue layer to be sutured, and a patient's anatomy, said radial diameters approximately ranging from 0.1 inches to 1 inch.

7. A device of claim 2 wherein said guide means integrally formed of high density polyethylene, and having an indice located in an upper surface of said distal end to properly align said passageways with respect to walls of the wound to be closed.

8. A device of claim 3 wherein said angles are generally between 5 and 15 degrees, and wherein a distance between said exit holes range between 0.10 inches and 0.75 inches.

9. A method of suturing an open wound comprising the steps of:

(a) providing a guide;

(b) grasping and inserting a tip means for passing suture material through a first passageway in said guide until reaching tissue and until said tip means is seen through the peritoneum by way of a surgical camera;

(c) releasing said suture material and withdrawing said tip means from said guide, and leaving the suture material in place;

(d) inserting said tip means in a second passageway defined within said guide and appositely adjacent directing said tip means to a point where the suture material first left the body;

(e) grasping said suture material with said tip means;

(f) retrieving said suture material with said tip means through said guide outside the wound; and (g) removing said guide means from the wound and tying ends of said suture material together to provide closure of the wound.

10. A method according to claim 9, wherein said guide comprises a longitudinal axis and distal and proximal ends, and further having an extending lip near said distal end of said guide means and being generally perpendicular to said longitudinal axis, and having a generally tapering portion toward said proximal end, said guide means defining therein at least one passageway therethrough at a first angle less than 90° from said longitudinal axis, and providing for exit holes above said lip and along said tapering portion, wherein said tapered end of said guide positionable within said wound with the lip portion above the wound to be closed and the surgical instrument carrying suture material passed through said passageway at said angle to the predetermined area within the body to assist in closing the open wound.

11. The method according to claim 10, wherein said second passageway through said guide means forming a second angle less than 90° from said longitudinal axis, and positioned appositely adjacent said first passageway, and further having exit holes above said lip and along said tapering portion, wherein the suture material can be left at the predetermined point within the body and the surgical tool and be inserted into the hole above said lip portion through the second passageway to retrieve the suture material from the area within the body.

12. The method according to claim 10, wherein said guide further comprises an extending finger adjacent to said tapered portion and generally symmetrical about said longitudinal axis extending a length sufficient to be accurately viewed and identified to provide a reference point while viewing any suturing procedure.

13. The method according to claim 10, wherein said distal portion of said guide comprises a concave radial surface to assist in gripping and positioning said guide means within said open wound.

14. The method according to claim 10, wherein said exit holes in said tapering portion are of sufficient longitudinal distance from said lip to accommodate the depth of the wound to be closed.

15. The method according to claim 10, wherein said guide means is provided in a plurality of sizes having different radial diameters and different longitudinal lengths between said lip and said exit holes in said tapering section to accommodate the depth of the wound to be closed and a patient's anatomy.

* * * * *